Figure 1:
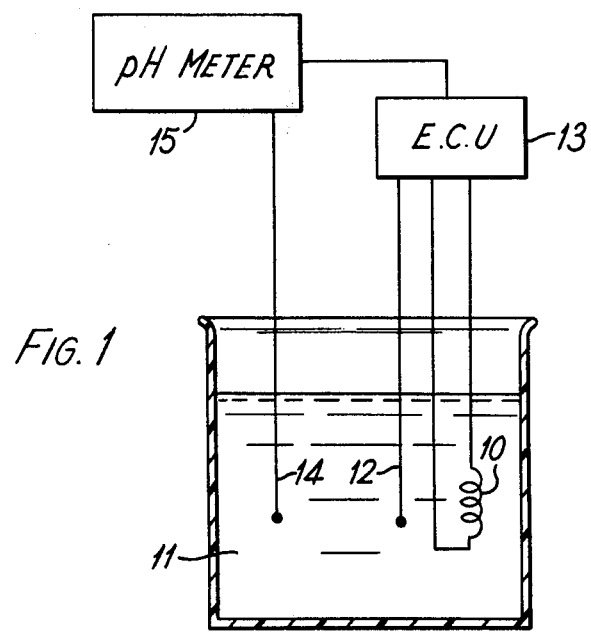

United States Patent [19]

Dobson

[11] 4,152,235
[45] May 1, 1979

[54] ION SELECTIVE ELECTRODE

[75] Inventor: John V. Dobson, Hartlepool, England

[73] Assignee: National Research Development Corporation, London, England

[21] Appl. No.: 811,845

[22] Filed: Jun. 30, 1977

Related U.S. Application Data

[63] Continuation-in-part of Ser. No. 488,244, Jul. 12, 1974.

[30] Foreign Application Priority Data

Jul. 18, 1973 [GB] United Kingdom ............... 34132/73
May 3, 1977 [GB] United Kingdom ............... 18452/77

[51] Int. Cl.² .......................................... G01N 27/46
[52] U.S. Cl. ................................ 204/195 M; 204/1 T
[58] Field of Search .......... 204/1 H, 1 T, 1 A, 195 M

[56] References Cited

U.S. PATENT DOCUMENTS 3,258,414  6/1966  Gregor et al. ................. 204/195 M
3,835,013  9/1974  Grubb et al. ................... 204/195 P

FOREIGN PATENT DOCUMENTS 397303  8/1933  United Kingdom .................... 204/1 H

OTHER PUBLICATIONS

Al Attar et al., "J. of Electroanalytical Chemistry", vol. 27, 1970, pp. 59–67.
Schwing et al., "Analytica Chemica Acta", vol. 15, 1956, pp. 379–388.
Dobson et al., "The Palladium–Hydride Reference Electrode in Hydrogen-Free Electrolyte Solutions at Elevated Temperatures", (Reprint of paper presented at an International Conference at the University of Surrey in England, Jan. 1973).

Primary Examiner—T. Tung
Attorney, Agent, or Firm—Cushman, Darby & Cushman

[57] ABSTRACT

An ion-sensitive electrode for measuring the concentration of a predetermined ion in a liquid is described which employs a metal hydride, such as palladium hydride, or a metal-alloy hydride in proximity with, or in contact with, a mixture of an acid and the salt of the acid with the predetermined ion. The hydride may be precharged with hydrogen or may be charged in situ.

17 Claims, 13 Drawing Figures

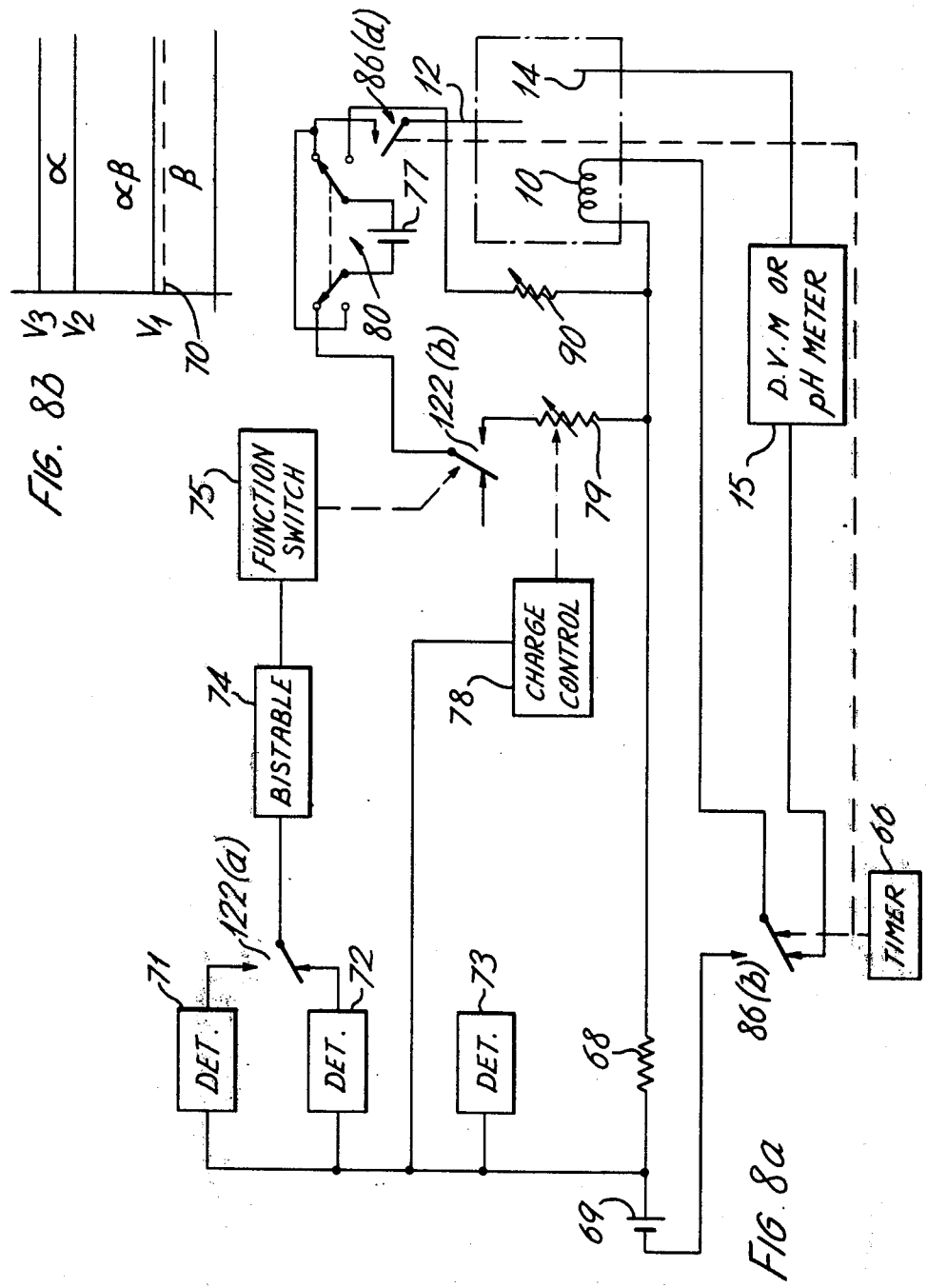

ION SELECTIVE ELECTRODE

CROSS-REFERENCE TO RELATED APPLICATION

This application is a continuation-in-part of my earlier application Ser. No. 488,244, filed July 12, 1974.

The present invention relates to ion selective electrodes which include a metal or metal alloy capable of forming a hydride, particularly but not exclusively palladium hydride. Such electrodes are used only when they also contain hydrogen and a hydride is present.

The present application is a continuation-in-part of U.S. application Ser. No. 488,244.

The absorption of considerable quantities of hydrogen in palladium and some other metals to form alloys known as hydrides is well known. Paladium hydride retains hydrogen for a considerable time at room temperature; for example an $\alpha+\beta$ paladium hydride electrode will remain in this phase for many days.

Provided the electrode is in the $(\alpha+\beta)$ phase, a palladium hydride electrode can be used to measure hydrogen ion concentration in aqueous solution in the same way as a conventional platinum-hydrogen electrode or a glass electrode.

In this specification, the term ion selective electrode means an electrode whose potential in a solution measured relative to a reference potential, depends on the concentration of a particular ion, or a particular group of ions, in the solution. Also in this specification and claims, the term "hydride" means a combination of hydrogen with a metal, the combination often being regarded as an alloy, in which hydrogen is apparently "absorbed" by the metal instead of forming a stoichiometric compound.

According to a first aspect of the present invention there is provided an ion selective electrode for use in measuring the concentration of an ion in a predetermined liquid or in any one of a number of predetermined liquids, including a material capable of forming a hydride, the material being a metal or a metal alloy and the hydride being as hereinbefore defined, and a mixture of an acid and the salt of the acid with the ion, the concentration of which is to be measured, the acid and the salt being substantially insoluble in the predetermined liquid or in the predetermined liquids and the mixture being positioned in proximity with the metal or the metal alloy.

According to a second aspect of the present invention there is provided an ion selective electrode for use in measuring the concentration of a predetermined ion in a predetermined liquid or in any one of a number of predetermined liquids, including a material capable of forming a hydride, the material being a metal or a metal alloy and the hydride being as hereinbefore defined, and a mixture of an acid and the salt of the acid with the ion, the concentration of which is to be measured, the acid and the salt being substantially insoluble in the predetermined liquid or in the predetermined liquids, and the mixture being so positioned in contact with the metal or alloy that the predetermined liquid, or one of the predetermined liquids can be made to contact both the mixture and the metal or alloy when ion concentration measurements are to be made.

The metal is preferably palladium, but other metals which can be used include yttrium, zirconium, titanium, vanadium, or alloys of palladium with one or more of these metals, or alloys of two or more of these metals. In operation the metal or alloy is either precharged with hydrogen or charged with hydrogen in situ.

Concentrations of the following ions: Ca, Mg, Sr, Ba, Y and La may, for example, be measured if, of course, a different electrode is provided for each ion. Each such electrode includes a mixture of stearic acid and the salt of that acid with the ion, the concentration of which is to be measured, the mixture being in close proximty with the palladium.

Advantageously the acid and salt chosen for the mixture should have a melting point such that the mixture remains solid at the highest temperature at which the electrode can be used in view of increase in loss of hydrogen at high temperatures.

According to a third aspect of the present invention there is provided a method of measuring the concentration of an ion in a solution using an electrode which includes a metal hydride as hereinbefore defined, or a metal alloy hydride as hereinbefore defined and a mixture of an acid and a salt of the acid with the ion the concentration of which is to be measured, the mixture being positioned in proximity with the metal hydride or the alloy hydride, and the acid and the salt being substantially insoluble in the solution, comprising the steps of contacting the solution with both the mixture and the metal hydride or the alloy hydride, at the same time contacting the solution with a reference electrode and measuring the potential between the ion selective electrode and a reference electrode while both electrodes are in contact with the solution.

The acid may be a fatty acid, provided it and its salt are insoluble in the predetermined liquid or liquids, and the following may be used (each acid/salt mixture is named and followed by the formula of the acid):

Stearic/Stearate —$CH_3(CH_2)_{16}COOH$
Lauric/Laurate —$CH_3(CH_2)_{10}COOH$
Myristic/Myristate —$CH_3(CH_2)_{12}COOH$
Palmitic/Palmitate —$CH_3(CH_2)_{14}COOH$
Margaric/Margarate —$CH_3(CH_2)_{15}COOH$
Tridecanoic/Tridecanate —$CH_3(CH_2)_{11}COOH$ According to a fourth aspect of the present invention there is provided a method of measuring the concentration of an ion in a solution using an electrode which includes a metal hydride as hereinbefore defined, or a metal alloy hydride as hereinbefore defined and a mixture of an acid and a salt of the acid with the ion the concentration of which is to be measured, the mixture being positioned in contact with the metal hydride or the alloy hydride, and the acid and the salt being substantially insoluble in the solution, comprising the steps of contacting the solution with both the mixture and the metal hydride or the alloy hydride, at the same time contacting the solution with a reference electrode, and measuring the potential between the ion selective electrode and a reference electrode while both electrodes are in contact with the solution.

As has been mentioned, in operation a hydride of the metal or the metal alloy must be present and therefore the electrode must be either charged before use, to an extent which allows the electrode potential to remain stable for a useful length of time, or arrangements must be made to supply hydrogen while the electrode is in use.

The supply of hydrogen may for example be electrolytic by the electrolysis, at intervals between ion concentration measurements, of the solution whose ion concentration is to be measured, or a different and separate electrolyte whose concentration is not being measured or the supply may be from a gas supply applied to part of the palladium which in operation is not immersed in the solution. The gas supply itself may include means for electrolysing a solution to provide hydrogen.

The control of the hydrogen supply may for example be at a steady rate such that the loss of hydrogen is substantially balanced, or monitoring means may be provided to determine the concentration of hydrogen in the palladium and the supply of hydrogen may be controlled in accordance with the output of the monitoring means either by controlling a rate of supply or by causing hydrogen to be supplied at intervals each time a low concentration limit is reached.

The monitoring means may measure the electrical resistance of the hydride in order to determine the concentration of hydrogen.

The hydrogen concentration is preferably maintained such that in an electrode employing palladium the hydrogen/palladium alloy remains in the $(\alpha + \beta)$ phase but operation in the $\beta$ phase is used for some electrodes.

The control means preferably includes means for applying a positive potential to the ion selective electrode with respect to a further electrode.

The positive pulses give rise to the following important advantages:

the electrode surface becomes self-cleaning since the pulses have the effect of liberating a small quantity of hydrogen from the palladium lattice and this hydrogen combines with the impurities or carries them away with it; and the effect of dissolved oxygen and reducible ions is practically eliminated since the hydrogen reacts with them and thus removes them.

Electrodes according to the invention may be used in solutions with solid suspensions since the self cleaning substantially prevents the fouling deterioration in performance and failure which occurs with glass electrodes.

Further electrodes according to the invention may be used in a system in which the electrolyte is flowing, that is it is constantly changed, or a system where the electrolyte static or flowing is open to the air so that oxygen becomes dissolved, or in a closed system where the electrolyte is static or flowing and continuous supplies of air are prevented from reaching the electrolyte.

Figure 2:
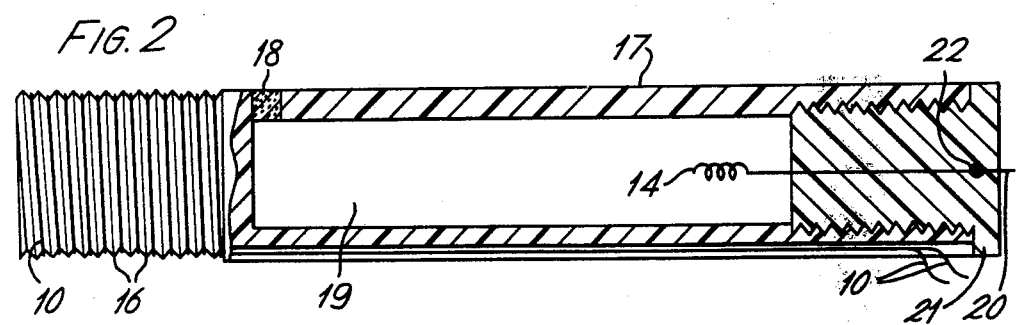
Figure 3:
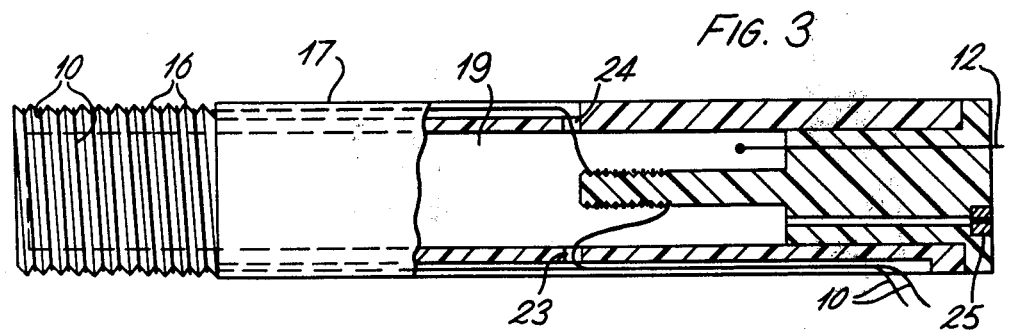
Figure 4:
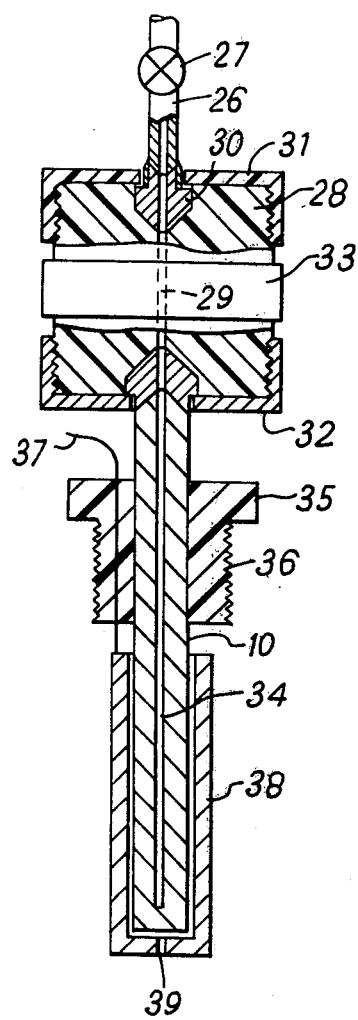
Figure 7:
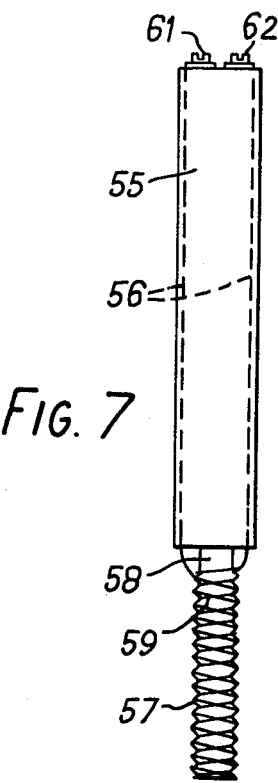
Figure 10:
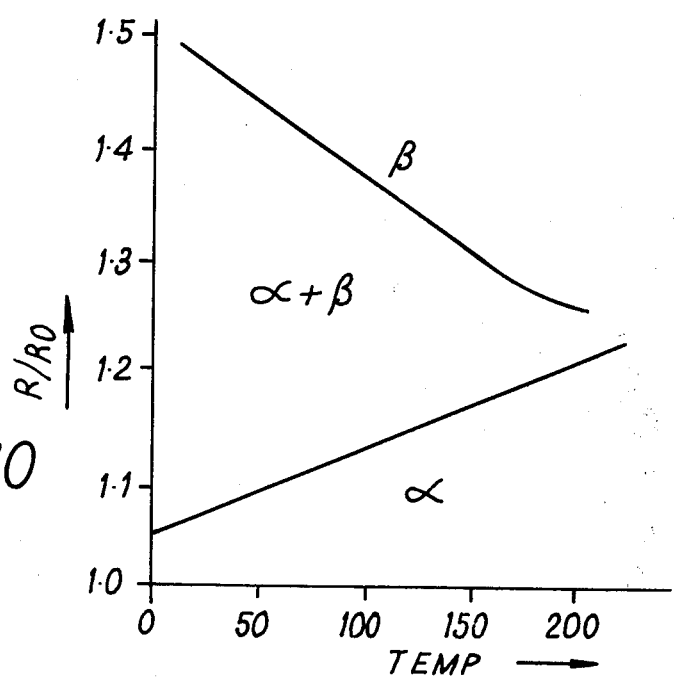
Figure 5:
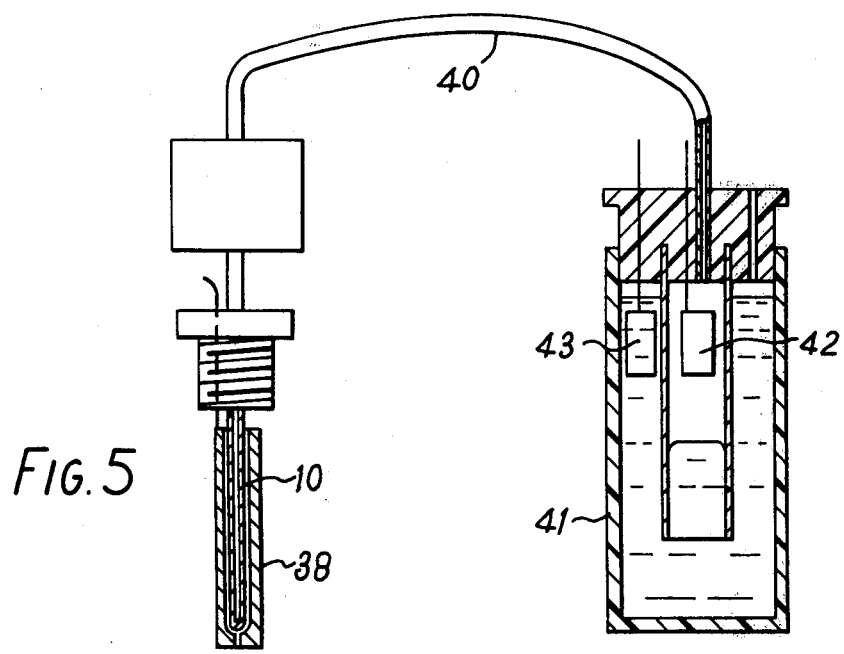
Figure 6:
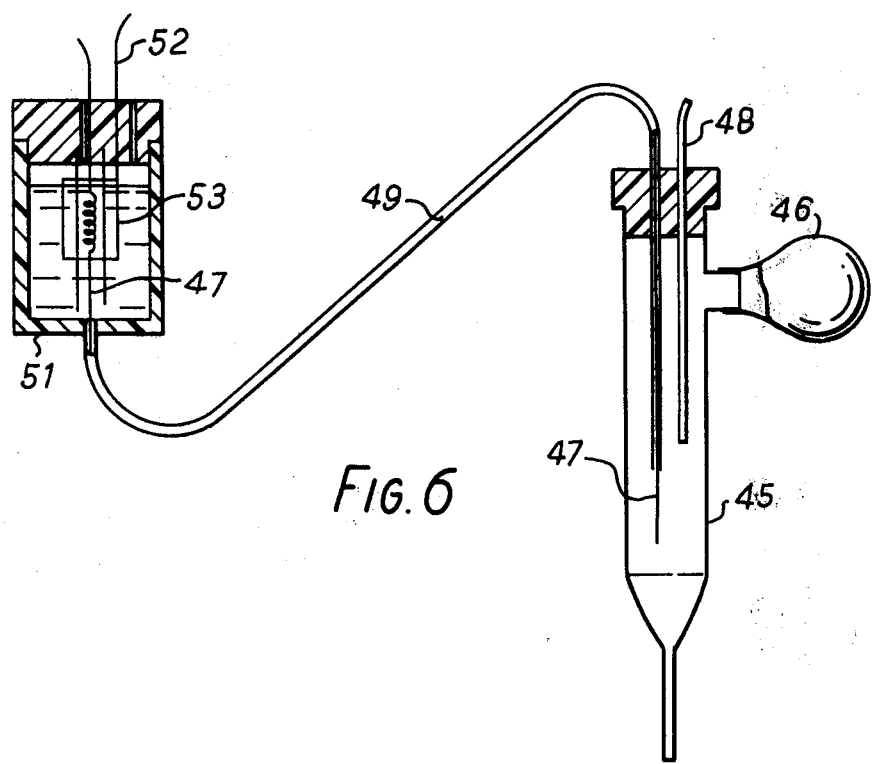
Figure 9:
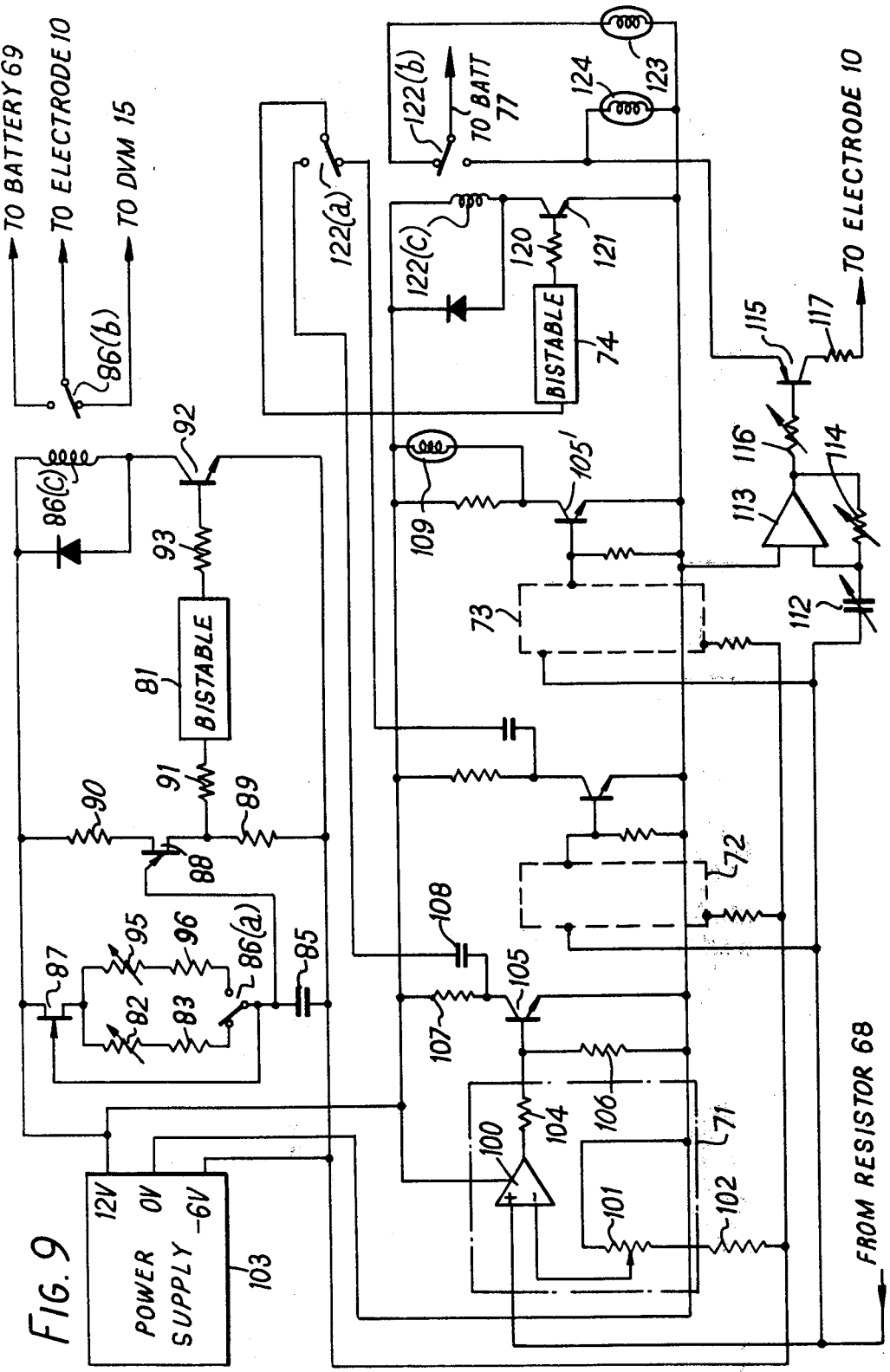
Figure 11:
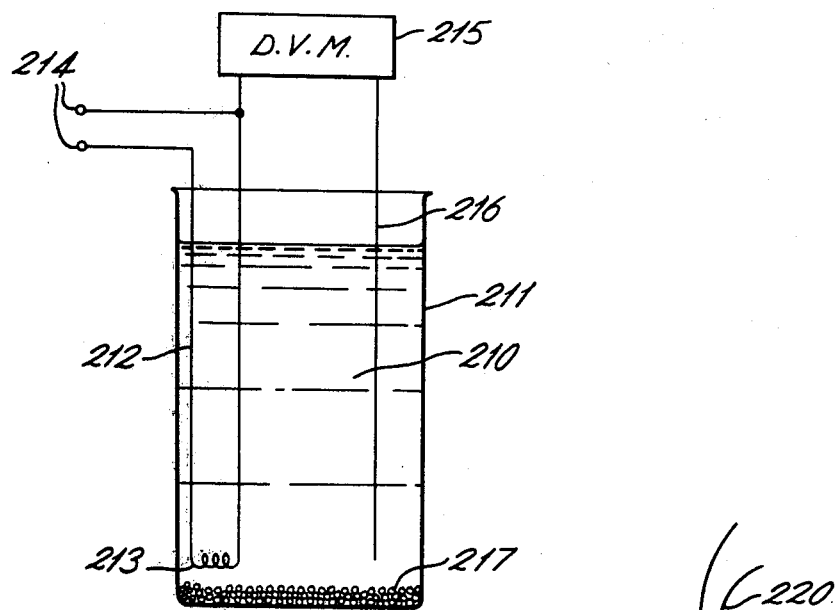
Figure 12:
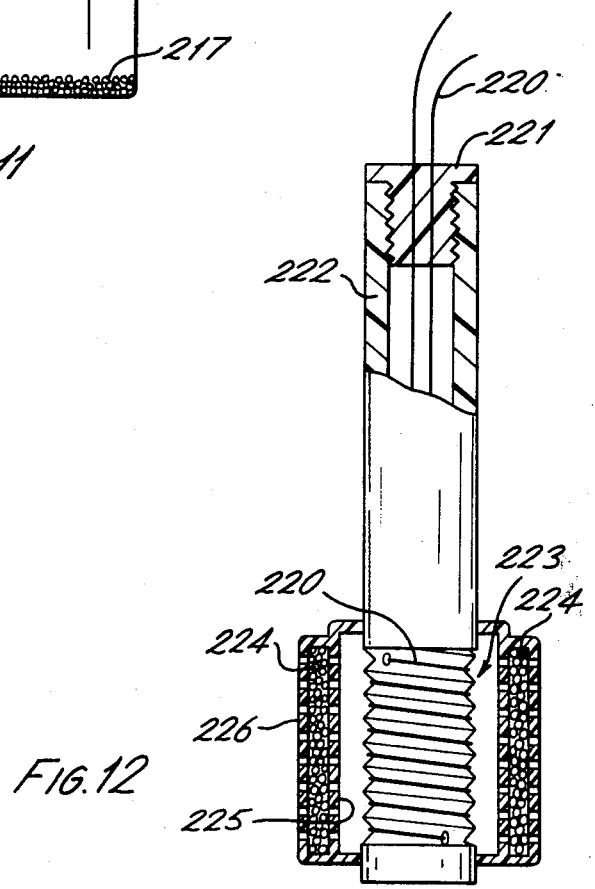

Certain embodiments of the invention will now be described by way of example with reference to the accompanying drawings in which:

FIG. 1 is a block diagram of apparatus for measuring the potential of palladium electrodes and for charging such electrodes with hydrogen, FIG. 2 is a schematic cross-section of a probe, which includes a palladium electrode and a reference electrode for use in the apparatus of FIG. 1, FIG. 3 is a schematic cross-section of a probe, for use with the apparatus of FIG. 1, which includes a palladium electrode, an electrolyte and an auxiliary electrode for charging the palladium electrode with hydrogen, FIG. 4 is a schematic cross-section of a probe, for use in a modified form of the apparatus of FIG. 1, which has a palladium electrode with an internal chamber, and means for passing hydrogen into the chamber, FIG. 5 is a schematic cross-section of a probe, for use in a modified form of the apparatus of FIG. 1, which has a palladium electrode with an internal chamber coupled to means for electrolysis to liberate hydrogen, FIG. 6 is a schematic cross-section of apparatus, including an ion sensitive electrode, for medical or biological applications, FIG. 7 is a schematic view of a first embodiment of an ion selective electrode according to the invention, FIG. 8(a) is a block diagram of the electrical control unit of FIG. 1, FIG. 8(b) is a graph illustrating the triggering voltages of detector circuits of FIG. 8(a), FIG. 9 is a part circuit diagram, part block diagram of the electrical control unit of FIG. 1, FIG. 10 is a graph showing the relation between palladium hydride phases and the electrical resistance of palladium hydride, FIG. 11 is a schematic diagram of a second embodiment of an ion selective electrode according to the invention, and FIG. 12 is a partial cross-section of a third embodiment of an ion selective electrode according to the invention.

In FIG. 1 a palladium wire electrode 10 is charged with hydrogen by the electrolysis of an electrolyte 11, the electrolysis being carried out between the palladium electrode 10 and an auxiliary platinum electrode 12. An electrical control unit 13 constantly measures the resistance of the palladium wire and in this way determines, as will be explained in more detail later, the concentration of hydrogen in the palladium. The control unit 13 causes electrolysis to take place when the desorption of hydrogen from the wire has reached a point when the palladium is about to leave the $(\alpha + \beta)$ phase.

Hydrogen ion concentration (pH value) measurements are carried out when electrolysis is not taking place by measuring the potential of the palladium wire electrode 10 with reference to the reference electrode 14 which may be, for example, a silver, silver chloride electrode. The potential of the electrode 10 depends upon the equilibrium between hydrogen in the alloy and hydrogen ions at the surface of the electrode and hence depends upon the hydrogen ion concentration of the electrolyte. The voltage between the electrodes 10 and 14 is measured by a pH meter (for example a specially graduated voltmeter) or digital voltmeter, or any other potential measuring device 15.

One practical form of the palladium electrode 10 and the reference electrode 14 is shown in FIG. 1. Palladium wire forming the electrode 10 is wound round threads 16 formed on a hollow PTFE body 17. The wire is insulated where it runs along a groove in the body 17 to the upper end of the body (to the right of FIG. 2). The wire is also insulated where it returns over the thread from the lower end of the body to the groove. A sintered PFTE plug 18 forms a porous electrolyte connection between the electrolyte outside the body and that contained in a cylinder chamber 19 within the body. The chamber 19 also contains silver chloride fused to a silver wire 20 to form an electrode 14. The wire 20 passes through a screwed PIFE plug 21 by way of a bead electrical seal 22. The probe formed by the apparatus of FIG. 2 is used in an electrolyte whose pH value is to be measured and the chamber 19 is also filled with this electrolyte type although other electrolytes such as hydrochloric acid could be used.

Electrolytic cathodic charging is used to maintain the hydrogen concentration in the wire 16 in the correct range and for this purpose a platinum or some other inert electrode is also placed in the electrolyte. Clearly the probe of FIG. 2 can only be used with an electrolyte which can be electrolysed to provide hydrogen. In addition the electrolyte must be flowing past the electrodes or be of large volume in order to prevent the electrolyses changing the pH value to be measured.

Another form of probe shown in FIG. 3 again has a palladium wire wound in threads 16 on the outside of a PTFE body 17 but in this case a palladium wire is taken in through seals 23 and 24 to the inner chamber 19 which in this case contains an electrolyte which can be electrolysed to provide hydrogen. As in FIG. 2 the wire is insulated where it is in grooves in the body between the thread, the seals 23 and 24, at the top of the probe, and the lower end of the thread.

Electrolysis to provide hydrogen is carried out between the wire 10 and the platinum wire 12 which is inside the chamber 19. A filler plug and air vent 25 is provided. The probe of FIG. 3 can thus be used with an electrolyte which cannot be electrolysed to provide hydrogen or an electrolyte which is not flowing, and in this case the reference electrode 14 (not shown in FIG. 3) is placed in the solution whose pH value is to be measured. The hydrogen libertated adjacent to that part of the wire 10 which is in the chamber 19 flows along the inside of the wire, in a way somewhat analogous to flow along a pipe, to maintain the required hydrogen concentration in that part of the wire which is wound on the exterior of the body 17. The wire 10 may in some cases be mainly within the chamber 19 with only a small portion on the outside of the body 17.

The electrical control unit 13 of FIG. 1 provides periodic anodic pulses between the electrodes 10 and 12 and these pulses "clean" the electrode in the way explained above. With the arrangement of FIG. 3 self-cleaning cannot be carried out by pulses between the auxiliary electrode 12 and the electrode 10, since the electrode 12 is in the chamber 19. Thus a separate auxiliary electrode is provided where cleaning is required.

In the form of the probe of FIG. 4 the hydrogen for the electrode is supplied through a copper or high pressure pipe 26 from a cylinder of hydrogen (not shown). In this case no auxiliary electrode 12 is provided since when hydrogen is required a valve 27 is opened by the control unit 13. A conical ended plug 30 is secured on to the copper pipe 26 and projects into a conical recess in a PTFE body 28 with a threaded exterior and a central bore 29. A brass cap 31 is screwed down on the PTFE body to make a firm connection between the pipe 26 and the body, and a similar joint between the body 28 and a silver palladium tube forming the electrode 10 is fixed firmly by a brass cap 32. A brass collar 33 surrounds the PTFE body 28 in order to strengthen it. Since the caps 31 and 32 are separated from the collar 33, the electrode 10 is electrically insulated from the pipe 26.

In FIG. 4 the electrode 10 is a silver/palladium alloy/rod with a small diameter bore 34 which connects through the bore 29 to the pipe 26. A PTFE plug 35, carrying a thread 36 allowing the probe to be screwed into a measurement cell, also holds a wire 37 which is connected to a platinum or palladium cylinder 38 fitted with a small intervening space round the electrode 10 throughout its length. A small aperture 39 allows the electrolyte to circulate freely between the electrode 10 and the cylinder 38. Measurement of the potential between the electrode 10 and the cylinder 38 provides an indication of the concentration of hydrogen. Thus the control unit 13 functions, not by resistance measurement, but in this case by potential measurement. Since the amount of hydrogen reaching the cylinder 38 from the electrode 10 depends on the amount of hydrogen emitted from the electrode 10 and the potential measured depends on the hydrogen concentration at the cylinder 38, the potential measured is a function of hydrogen concentration in the electrode 10. Hence by measuring this potential, the emission of hydrogen from the electrode 10 is measured and this emission depends on hydrogen concentration in the electrode 10.

Where the use of a high pressure gas supply is not appropriate, the apparatus of FIG. 5 may be used. This comprises a thin walled palladium/silver alloy membrane forming the electrode 10. This membrane in tubular form is connected to a pipe 40 by the same type of insulating connector as is shown in FIG. 4. The pipe 40 enters a PTFE container 41 containing an electrolyte which can be electrolysed to liberate hydrogen when current is passed between a platinum electrode 42 and a further platinum electrode 43. The control unit 13 causes electrolysis to be carried out in the container 41 when potential measurements between the cylinder 38 and the electrode 10 indicate that the hydrogen concentration in the membrane 10 is low. As before a space exists between the cylinder 38 and the electrode 10 allowing electrolyte to circulate freely.

As electrolysis proceeds the hydrogen released pushes the electrolyte level down in the region of the electrode 42 as shown. Electrolysis then ceases until the hydrogen has sufficiently desorped from the electrode 10 for the electrolyte level to rise again. Thus a regulating mechanism is set up which may possibly be used instead of the control unit 13 but preferably in addition to the unit 13.

The electrodes of FIGS. 4 and 5 may be modified for control by resistance measurement by making the walls of the electrode 10 (with its internal bore) from alternate strips of PTFE and palladium; that is, viewed in horizontal cross-section, arcs of palladium are separated by arcs of PTFE. The low resistance of the electrode is increased by connecting the palladium strips in series and the cylinder 38 is no longer required.

The hydrogen concentration is not monitored in the arrangement shown in FIG. 6. Here a glass container 45 with a rubber teat 46 contains a palladium wire electrode 47. The apparatus of FIG. 6 is used for biological or medical purposes and the liquid whose pH value is to be measured is drawn into the container 45 using the teat. A cannela 48 filled with electrolyte connects the interior of the container 45 to a reference electrode. The wire 47 is surrounded by fine bore PTFE flexible tubing 49 which projects for some distance into the container 45 and also protects the wire between the container 45 and a further PTFE container 51. In addition the tube 49 prevents loss of hydrogen along the wire 47. The palladium wire 47 extends the top of the container 51 as does a platinum wire 52 which is connected to a platinum cylinder 53. A small battery (not shown) is connected between the wires 47 and 52 and electrolysis of an electrolyte 54 is carried out continuously to liberate hydrogen and allow it to be absorbed by the wire 47 at a rate substantially equal to desorption from the wire along its full length but mainly in the container 45. Vents are provided to allow oxygen to escape from the container 51. Thus in the arrangement of FIG. 6 the hydrogen concentration is constantly maintained at the required level (that is such that the electrode potential remains constant when measured in a solution having a constant hydrogen ion cencentration) by the constant absorption of hydrogen in the container 51. Potential measurements for pH value are, of course, made between the wire 47 and the reference electrode.

In addition to its use for measuring pH values, the present inventor has found that the palladium hydride electrode can be used to measure the concentrations of some other ions. For example the palladium hydride electrode can be made responsive to calcium, magnesium, strontium, barium and yttrium ions in an aqueous electrolyte if the palladium wire or palladium cylinder is coated with a mixture of a fatty acid and its salt of the ion whose concentration is required.

An ion selective electrode responsive to calcium is shown in FIG. 7 where a solid PTFE body 55 has longitudinal grooves 56, and threads 57 cut in a portion 58 of reduced diameter. A thin coating of melted mixture of 50% stearic acid and 50% calcium stearate is applied by way of brush to the PTFE former. The threads cut into the PTFE former and help to retain the mixture when cold. A palladium wire 59 is then wound from a screw 61 along the threads and back up over the portion 58 diagonally to the threads and back along the grooves 56 to a screw 62. The mixture is then used to coat the palladium wire at the intersections where the "go" and "return" wires cross but other portions of the palladium wire are left exposed. However, the wire is wound under tension so that the main part of the wire is embedded in the mixture. The conrol unit 13 is used to measure the resistance of the wire and the wire can be charged with hydrogen by electrolysis in the way previously described through those parts of the wire which are not covered with the mixture.

Alternatively, the wire can be charged either before use, or in situ, from a remote source with the wire extended and acting as a duct for hydrogen in a similar way to the wire 47 of FIG. 6.

Such an ion selective electrode can be made sensitive to other ions simply by using other stearates, having the appropriate ion instead of calcium in the mixture.

The electrodes of FIGS. 2 to 6 can also be made selective to other ions by use of such a mixture either in contact with, or in proximity with, the hydride, provided the electrolyte being measured can make contact with both the acid/salt mixture and the hydride.

The electrical control unit 13 will now be described in more detail. In FIG. 8a the palladium wire electrode 10 is connected through relay contacts 86(b) to the D.V.M. or pH meter 15, the other side of which is connected to the reference electrode 14. The operation of the contacts 86(b) is under the control of a sequential timer 66. The timer operates to connect the D.V.M. for, for example, three minutes and then to disconnect the meter for ten seconds. This cycle is continually repeated to alternately allow pH measurement and the measurement of the resistance of the palladium wire.

The contacts 86(b) in their other position complete the circuit for measuring the resistance of the palladium, these contacts being connected in series with the palladium wire electrode 10, a resistor 68 and a battery 69. Since the voltage across the resistor 68 depends on the current from the battery 69, this voltage indicates the resistance of the palladium wire electrode 10. The voltage across the resistor 68 is applied to three detector circuits 71, 72 and 73. Where the electrodes of FIGS. 4 and 5, or similar electrodes, are used, the resistor 68 and the battery 69 are not required. The voltage between the electrode 10 and the cylinder 38 is applied to the detectors 71, 72 and 73 by way of the contacts 86(b).

The detector 71 provides an output voltage when the voltage across the resistor 68 falls below a voltage $V_1$ (see FIG. 8(b)) just above the boundary 70 between the $\beta$ and the $\alpha\beta$ phases, indicating that the palladium is about to enter the $\beta$ phase. As the voltage across the resistor 68 rises it is an indication first that the palladium has entered the $(\alpha+\beta)$ phase and as the voltage rises further that it has entered the $\alpha$ phase. The $\alpha$ phase is the phase in which the palladium contains insufficient hydrogen for a steady potential and the $(\alpha+\beta)$ phase is the phase in which the electrode should operate.

The detector 72 is set to provide an output signal when a voltage $V_2$ (see FIG. 8(b)) is reached that is when the palladium hydride enters the $\alpha$ phase from the $(\alpha+\beta)$ phase.

The detector 73 provides an output signal when the voltage across the resistor 68 rises to $V_3$ indicating that the palladium hydride has already entered the $\alpha$ phase and the system is now out of limits of useful operation.

The outputs of the detectors 71 and 72 are connected to contacts 122 (a) of a relay operated by the output of a bistable circuit 74. Thus if the detector 71 is connected to the bistable circuit 74 through the contacts 122(a) and the detector 72 operates, then the contacts 122(a) connect the detector 72 to the bistable circuit 74. When the voltage $V_2$ is exceeded the detector 71 once more becomes connected to the bistable 74. When the detector 71 has just operated, the bistable circuit enters a state in which a function switch 75 operates an indicator lamp indicating that the palladium is in the $\beta$ phase. When the detector 72 has just operated the bistable circuit enters its other state in which the function switch 75 operates contacts 122(b) connecting an electrical source 77 shown in FIG. 8(a) as a battery to the palladium electrode 10 so that current passes between the electrode 10 and the auxiliary electrode 12 charging the palladium hydride with hydrogen. At the same time a lamp connected to the function switch 75 indicates that charging is taking place. Further relay contacts 86(d) controlled by the timer 66 prevent electrolysis taking place when the measuring device 15 is connected by the contacts 86(b).

The detector 73 lights a warning lamp when the voltage $V_3$ is exceeded as an indication that the rate of charging may not be sufficient to make up hydrogen loss and should be increased.

The connection of the battery 77 is by way of a six pole reversing switch 80 which allows positive pulses for cleaning the electrode 10 to be generated manually when required. A variable resistor 90 allows the cleaning current which flows in the opposite direction to the charging current to be adjusted.

A transistor shown in FIG. 8a as a variable resistor 79 is controlled by a circuit 78 to adjust the rate of charging between the electrodes 10 and 12 in dependence upon the rate of loss of hydrogen. The rate of loss is sensed by differentiating the voltage across the resistor 68.

The $(\alpha+\beta)$ phase extends over a reduced range of hydrogen concentration in palladium as temperature rises. Thus although the change in resistance of palladium with hydrogen concentration is nearly linear throughout most of the range of interest the voltages which the detectors 71, 72 and 73 operate should be set with the temperature range of operation of the electrode in mind.

FIG. 10 is a graph showing the boundaries of the α, β and (α+β) phases in terms of the normalised palladium wire resistance R $R_o$, $R_o$ being the resistance of a palladium wire which does not contain hydrogen.

A typical sequence of operation is as follows assuming that the sequence starts with the hydride in the β phase, the detector 71 operated, and therefore with the detector 72 connected to the bistable circuit 74. As the hydrogen desorbs, the hydride passes into the (α+β) phase allowing measurements to be made, and then into the α phase when the detector 72 operates. Charging now begins and continues each time the contacts 86(b) operate until the detector 71, now connected to the bistable circuit 74, again operates and the cycle is repeated. Should the rate of charging be insufficient to reach the β or (α+β) phase, the detector 73 operates and an adjustment to the time constant of the charge control circuit 78 can be made.

The apparatus of FIG. 8(a) is initially calibrated by adjusting, by means of zero and full scale adjustments of the measuring device, the response of the apparatus to solutions of known pH.

The various circuits of FIG. 8(a) are shown in more detail in FIG. 9.

The timer 66 operates by charging and discharging a 100 μFarad capacitor 85. With the contacts 86(a) of a relay in the position shown, the capacitor 85 charges through a type MRN5454 field effect transistor 87, a variable resistor 82 and 100 Kohm resistor 83 until it reaches a point where a type 2N2646 unijunction transistor 88 conducts discharging the capacitor 85 by way of a 100 ohm resistor 89. The voltage developed across this resistor is applied through a 10 Kohm resistor 91 to a bistable circuit 81. The transistor 88 has a 220 ohm base resistor 90.

The application of the pulse to the bistable circuit switches on a BF156 transistor 92 by way of a 3.0 Kohm resistor 93 and thus current passes through the coil 86(c) of a relay switching over the contacts 86(a). Thus the capacitor now starts to charge through the FET87 at a rate determined by variable potentiometer 95 and a 10 Kohm resistor 96. In this way the sequential timer circuit oscillates setting and resetting the bistable circuit 81 and in so doing operates the contacts 86(b) of FIG. 8(a). The reset time of the circuit in the "measure" and "charge" states can be adjusted using the resistors 82 and 95.

Another form of timer which may be used is the NE555V timer chip integrated circuit.

The detector circuits 71, 72 and 73 each consist of the same basic circuit and for this reason only the detector 71 will be described in detail. A type LM710CN operational amplifier 100 is connected as a comparator, receiving the voltage from the resistor 68 at its non-inverting input. A reference voltage is applied to the inverting input from a 1 Kohm pre-set potentiometer 101 connected in series with a 4.7 Kohm resistor 102 connected to a −6 volt terminal of a power supply 103. Other voltages applied to the detectors are as shown in FIG. 9. The output of the comparator 100 is connected through a 1 Kohm resistor 104 to the base of a type BC108 transistor 105. A 100 Kohm base bias resistor 106 is connected between the base of the transister 105 and the 0 volt of the power supply. A 1.5 Kohm resistor 107 is connected between the +12 volt rail and the power supply and the collector of the transistor 105 as a load resistor and the voltage developed across this load is coupled to the contacts 122(a) by way of a 2,200 pF capacitor 108.

The detector 72 is coupled in the same way to the contacts 122(a) but in the detector 73 the output of the transistor 105' is connected by way of a red warning light 109 to the 12 volt rail to indicate when rate of charge may be too low.

As an alternative to using three LM710CN operational amplifiers, two of these amplifiers may be replaced by a sinlge SN72720 integrated circuit which includes two operational amplifiers.

In the circuit 78, the voltage across the resistor 68 is differentiated by a variable capacitor 112 and a type 741 operational amplifier 113 with a variable feedback resistor 114. The output of the amplifier 113 is applied to a transistor 115 by way of a variable resistor 116. This transistor and its emitter resistor 117 form the resistor 79 of FIG. 8(a). Thus the current passing between the electrodes 10 and 12 depends on the voltage applied to the base of the transistor 115 which is in turn determined by the differential of the voltage across the resistor 68.

The output of the bistable 74 is connected by way of a 3.9 Kohm resistor 120 to the base of a type D42C3 transistor 121. The collector of this transistor is connected to the coil 122(c) of a relay which has the two sets of contacts already mentioned: 122(a) and 122(b). The contacts 122(a) are connected at the input to the bistable circuit 74 to connect the output of either the detector 71 or the detector 72 in turn to the bistable circuit 74. The contacts 122(b) are used to disconnect the battery 77 that is used to charge the palladium electrode when the detector 71 triggers. At the same time a lamp 123 is switched into circuit to indicate the hydrogen content of the palladium is sufficient for measurements. The contacts 122(b) also switch in a lamp 124 when the detector 72 triggers to indicate that the palladium electrode is being charged with hydrogen.

If either of the lamps 123 or 124 is on measurements can proceed since the hydride is in the (α+β) phase, or just in the α or β phase temporarily. When the lamp 109 is on measurements should not proceed.

In FIG. 8(a) the battery 77 and the switch 80 may be replaced by a pulse generator which provides both negative charging pulses and positive cleaning pulses each time the contacts 122(b) are closed. The pulse rate required for cleaning depends on the amount of cleaning necessary and therefore on the electrolyte. Usually positive pulses at a rate of between one every second and one every several minutes will be sufficient. These pulses in addition to replacing hydrogen and cleaning the electrode, also remove oxygen and remove reducible ions in the way described above.

Alternatively, a manual switch (not shown) may be inserted in series with the battery 77 to allow charging to be carried out, when the lamp 124 lights, as a series of pulses generated manually by intermittent operation of the switch.

With the arrangement of FIG. 8(a) should the detector 73 and the lamp 109 indicate that the rate of charging is insufficient the capacitor 112 and the resistor 114 can be varied to increase the rate of charge by varying the time constant of the differentiating circuit. Means may however be provided to carry out this variation automatically in dependence upon the output of the detector 73.

As has been mentioned, the electrodes of FIGS. 4 and 5 may be operated in the β phase and this is useful where a zero electrode potential is required. For a given electrode potential the range of hydrogen concentration is comparatively small and therefore the hydrogen concentration has to be carefully controlled. The potential between the cylinder 38 and the electrode 10 allows precise control but different settings for the voltages at which the detectors 71, 72 and 73 operate are required. Instead a different detector circuit arrangement may, as with the other electrodes described, be used.

In FIG. 11 a solution 210 containing calcium ions, the concentration of which is to be measured, is held by a beaker 211. A palladium hydride electrode 212 is formed from a piece of palladium wire containing a coiled portion 13. The palladium wire may be precharged with hydrogen or may be charged in situ by using one of the methods described above. Terminals 214 are provided for the palladium wire so that its resistance can be monitored and charging with hydrogen, for example by electrolysis, may be carried out when the resistance of the wire indicates that the hydrogen content is low. A digital voltmeter (DVM) 215 is connected to the palladium hydride electrode 212 and to a reference electrode 216 shown schematically which may be of any appropriate known type such as a calomel electrode. The bottom of the beaker 211 contains a mixture of 50% stearic acid and 50% calcium stearate in the form of granules adjacent to the coil of palladium wire 213.

The concentration of calcium ions in the solution 210 is measured by observing the voltage difference between the palladium hydride electrode and the reference electrode 216. After the solution has been placed in the beaker, some time will be required before the voltage reading obtained from the DVM 215 settles down and in order to reduce this time a magnetic stirrer (not shown) may be placed in the beaker with its drive unit underneath. Solubility equilibrium is then achieved relatively quickly between stearic salts, the solvent and the ions to be measured. The voltage readings obtained from the DVM are compared with a calibration curve for the system previously prepared by plotting voltage against calcium ion concentration for known concentrations.

The arrangement of FIG. 11 can only be used where pH is known and constant since, as is mentioned below, the palladium hydride electrode measures proton concentration resulting from an equilibrium set up between ions of the mixture and the ion whose concentration is to be measured. Therefore the "background" concentration of proton in the electrolyte must be taken into account when the voltage measurements are taken and this is achieved by using a calibration curve for the appropriate pH value.

In FIG. 12 a palladium wire 220 passes through a screwed plug 221 into the interior of a hollow PTFE former 222 with a threaded end portion 223. The wire 220 emerges from the interior of the former and passes round the threaded portion as shown. Granules of 50% stearic acid and 50% magnesium stearate mixture 224 are contained in a chamber formed by cylindrical grids 225 and 226 surrounding the threaded portion of the former 222. The grid structure can be formed from any rigid non-conducting material such as PTFE and may be a push-fit on the PTFE former 222 so that several different grid structures containing different acid/salt mixtures may be mounted on a former at different times giving an electrode sensitive to various ions.

The grid structure is designed to allow solubility equilibrium of the various ions to be achieved in the space between the grid 225 and the portion 223 of the former 222 without unduly restricting the flow of electrolyte through the grid which would result in the liquid in the space being unrepresentative of the electrolyte around the outer grid 226.

The concentration of magnesium ions may be measured by dipping the probe of FIG. 12 into an electrolyte containing the ions and measuring the voltage difference between the palladium wire 220 and a reference electrode also inserted in the electrolyte. As before the palladium wire is either precharged with hydrogen or charged in situ and for the latter purpose the resistance between the two ends of the wire 220 may be monitored to provide an indication of the concentration of hydrogen in the wire.

The arrangement of FIG. 12 can be used where the electrolyte has a constant known pH, when the reference electrode may again be a calomel electrode and an appropriate calibration curve is used. Alternatively the pH of the electrolyte may vary and it is then necessary to use a pH sensitive electrode as the reference electrode. For example the reference electrode may be a glass electrode or preferably one of the palladium hydride electrodes described in connection with FIGS. 2,3,4 or 5. Variations in the pH of the electrolyte are then automatically taken into account by what is, in effect, a differential system.

In preparing other electrodes similar to those of FIGS. 11 and 12, the acid/salt mixture may be heated until melted and then poured into a flexible porous container such as a nylon gauze, linen or even paper. The flexible container is held in a desired shape until the mixture has become solid when the mixture plus container can be removed and positioned either in close proximity to the coil 213 or palladium wire or around the end portion of the former 222 but spaced therefrom.

The ion selective electrodes of FIGS. 11 and 12 can, of course, be made sensitive to other ions simply by using other stearates, having the appropriate ion instead of calcium or magnesium in the mixture. Indeed these electrodes can be made responsive to strontium, barium, yttrium and lanthium in aqueous electrolytes if the palladium wire is used in close proximity with a fatty acid and its salt of the ion whose concentration is required.

The operation of ion selective electrodes based on glass electrodes is described in a paper by Attar and Beck entitled "Alkaline Earth and Lanthanum Ion Electrodes of the Third Kind based on the Hydrogen Ion-Responsive Glass Electrode", published in the Journal of Electro-Analytical Chemistry and Interfacial Electrochemistry, 27 (1970) pages 50 to 67. It is throught that the palladium hydride electrode when used in close proximity with one of the above mentioned mixtures operates in a way which is analagous to the ion selective electrodes of the paper.

Briefly the electrodes are believed to operate as follows. An equilibrium is set up between the ions to be measured and ions formed when the fatty acid and salt ionise. The resulting concentration of proton depends on the concentration of the ion of interest and using the palladium hydride electrode to measure proton concentration indirectly measures the required concentration.

Although specific forms of the invention has been described it will be appreciated that many other forms of the invention are possible, the only essentials being that the hydride and the mixture of an acid and its salt are near to, or in contact with, one another.

I claim:

1. An ion selective electrode for use in measuring the concentration of an ion in an electrolyte including a metal or metal alloy having absorbed therein a quantity of hydrogen so as to form a hydride but not forming a stoichiometric compound therewith, and a mixture of a fatty acid and the salt of the acid with the ion, the acid and the salt being substantically insoluble in said electrolyte to allow the concentration of the said ion to be measured, and the mixture being positioned in proximity with the metal or the metal alloy.

2. An ion selective electrode according to claim 1 wherein the metal is chosen from the group consisting of palladium, yttrium, zirconium, titanium and vanadium.

3. An ion selective electrode according to claim 1 wherein the alloy comprises at least two metals from the group consisting of palladium, yttrium, zirconium, titanium and vanadium.

4. An ion selective electrode according to claim 1 including means for charging the metal or metal alloy with hydrogen while the electrode is in contact with the electrolyte.

5. An ion selective electrode according to claim 1 wherein the hydride has a hydrogen concentration within a range over which the electrode potential remains substantially constant for an interval sufficient for measurements to be made.

6. An ion selective electrode according to claim 1 wherein the mixture includes a stearic acid and a salt of the acid.

7. An ion selective electrode according to claim 1 wherein the salt is a salt of stearic acid with one of the following ions: Ca, Mg, Ba, Y, Sr, and La.

8. An ion selective electrode according to claim 1 wherein the metal or metal alloy is in the form of a wire wound in spaced apart turns around a generally cylindrical inert body and the said mixture is positioned in a container around but spaced from that part of the inert body carrying the wire, the container allowing electrolyte to pass from the exterior thereof to the mixture and allowing electrolyte to reach the said wire.

9. An ion selective electrode for use in measuring the concentration of a predetermined ion in an electrolyte including a metal or metal alloy having absorbed therein a quantity of hydrogen so as to form a hydride but not forming a stoichiometric compound therewith, and a mixture of a fatty acid and the salt of the acid with the ion, the acid and the salt being substantially insoluble in said electrolyte to allow the concentration of the said ion in said electrolyte to be measured, and the mixture being so positioned in contact with the metal or alloy that the electrolyte can be made to contact both the mixture and the metal or alloy when ion concentration measurements are to be made.

10. An ion selective electrode according to claim 9 wherein the said mixture forms a partial coating for the metal or metal alloy.

11. An ion selective electrode according to claim 10 wherein the metal is chosen from the group consisting of palladium, yttrium, zirconium, titanium and vanadium.

12. An ion selective electrode according to claim 10 wherein the alloy comprises at least two metals from the group consisting of palladium, yttrium, zirconium, titanium and vanadium.

13. An ion selective electrode according to claim 10 including means for charging the metal or metal alloy with hydrogen while the electrode is in contact with the electrolyte.

14. An ion selective electrode according to claim 10 wherein the hydride has a hydrogen concentration within a range over which the electrode potential remains substantially constant for an interval sufficient for measurements to be made.

15. An ion selective electrode according to claim 9 wherein the mixture includes a stearic acid and a salt of the acid.

16. An ion selective electrode according to claim 10 wherein the salt is a salt of stearic acid with one of the following ions: Ca, Mg, Ba, Y, Sr, and La.

17. An ion selective electrode according to claim 10 including an inert cylindrical member having at least one groove in the surface thereof, a coating of the mixture on the said surface, and a wire wound round the member over the coating, the wire being formed from the said metal or metal alloy, and the mixture being applied to portions of the wire.

* * * * *

Disclaimer 4,152,235.—*John V. Dobson*, Hartlepool, England. ION SELECTIVE-ELECTRODE. Patent dated May 1, 1979. Disclaimer filed June 29, 1981, by the assignee, *National Research Development Corp.*

Hereby enters this disclaimer to claims 1–17, inclusive of said patent.
[*Official Gazette Sept. 15, 1981.*]